(12) United States Patent
Piasini et al.

(10) Patent No.: US 9,592,106 B2
(45) Date of Patent: Mar. 14, 2017

(54) HOLLOW SUPERSTRUCTURE FOR A DENTAL PROSTHESIS

(71) Applicants: Bruno Piasini, Montagna in Valtellina-Sondrio (IT); Antonio Maria Scotti, Monza-Monza e Brianza (IT)

(72) Inventors: Bruno Piasini, Montagna in Valtellina-Sondrio (IT); Antonio Maria Scotti, Monza-Monza e Brianza (IT)

(73) Assignee: HERAEUS KULZER GMBH, Hanau (DE)

( * ) Notice: Subject to any disclaimer, the term of this patent is extended or adjusted under 35 U.S.C. 154(b) by 0 days.

(21) Appl. No.: 14/649,548

(22) PCT Filed: Nov. 27, 2013

(86) PCT No.: PCT/EP2013/003588
§ 371 (c)(1),
(2) Date: Jun. 3, 2015

(87) PCT Pub. No.: WO2014/094966
PCT Pub. Date: Jun. 26, 2014

(65) Prior Publication Data
US 2015/0313694 A1 Nov. 5, 2015

(30) Foreign Application Priority Data
Dec. 18, 2012 (EP) .................................. 12197754

(51) Int. Cl.
A61C 5/08 (2006.01)
A61C 13/271 (2006.01)
A61C 8/00 (2006.01)

(52) U.S. Cl.
CPC ................ *A61C 13/26* (2013.01); *A61C 5/08* (2013.01); *A61C 8/00* (2013.01)

(58) Field of Classification Search
CPC .............. A61C 13/26; A61C 8/00; A61C 5/08
See application file for complete search history.

(56) References Cited

U.S. PATENT DOCUMENTS

| 5,090,903 A | 2/1992 | Taylor et al. |
| 5,927,972 A * | 7/1999 | Humboldt ................ A61C 5/08 433/141 |
| 2012/0220986 A1* | 8/2012 | Wolff .................. A61M 31/002 604/892.1 |

FOREIGN PATENT DOCUMENTS

| DE | 831866 C | 2/1952 |
| DE | 4135861 A1 | 5/1993 |
| DE | 20112461 U1 | 1/2002 |
| EP | 0230294 A2 | 7/1987 |
| EP | 1652491 A1 | 5/2006 |

* cited by examiner

*Primary Examiner* — Glenn Richman
(74) *Attorney, Agent, or Firm* — Themis Law

(57) ABSTRACT

A superstructure for oral, dental and maxillofacial prostheses includes at least one anchoring dental element and at least one additional dental element, wherein the additional dental element has an internal hollow portion forming a closed cavity inside the same element. With respect to the known technology in the field, the superstructure of the invention offers the advantage of being lighter, more comfortable and less bothersome for the user, thanks to the substantial reduction in weight due to the smaller quantities of material used for producing it.

4 Claims, 3 Drawing Sheets

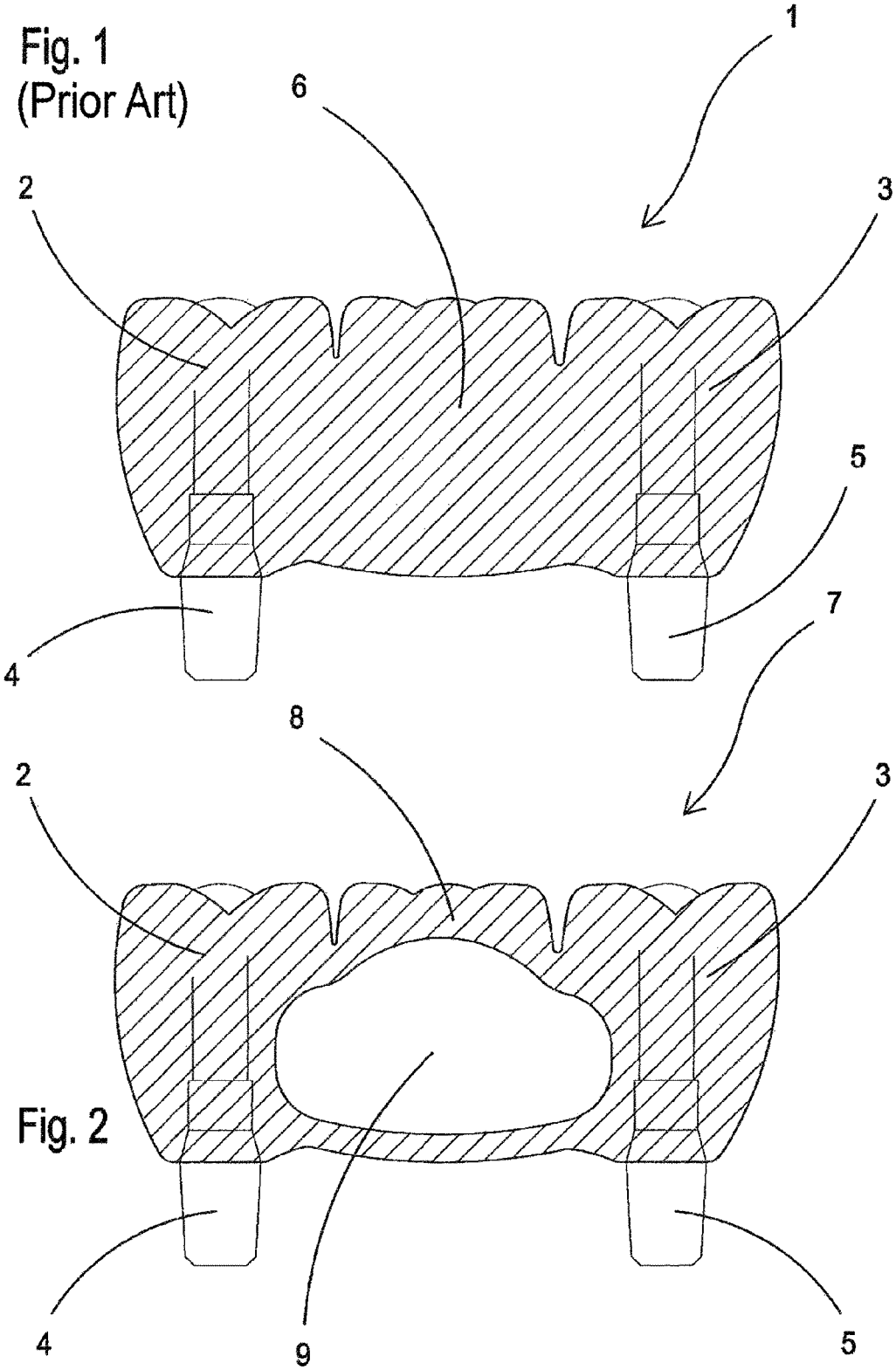

HOLLOW SUPERSTRUCTURE FOR A DENTAL PROSTHESIS

The present invention relates to a hollow superstructure for oral, dental and maxillofacial prostheses.

FIELD OF THE INVENTION

The field of application of the invention relates to superstructures normally used for restoring the morphology of the mouth, in substitution of natural teeth.

These superstructures generally consist of prostheses that reproduce the form of the teeth to be replaced, made of material resistant to mastication and coated with composite or ceramic materials. The anchorage of these superstructures in the patient's mouth is effected either with screws coupled with the implant, or by cementation of the prosthesis on stumps.

BACKGROUND OF THE INVENTION

Traditional superstructures in the form of a bridge have intermediate and extension dental elements composed of filled or solid bodies. For this reason, these known superstructures have the disadvantage of having a weight which makes them particularly uncomfortable and bothersome to wear in the user's oral cavity.

Furthermore, the solid structure of the intermediate and extension dental elements of known superstructures favors the transmission of heat and cold directly inside the mouth, thus creating further discomfort for the user, A further drawback of traditional superstructures with completely filled or solid intermediate and extension dental elements lies in the necessity of using and working with quantities of material that are excessive with respect to those strictly necessary for the structural functionality of these systems, with a useless waste of raw material, operating times and relative costs.

DE 4135861 A discloses a superstructure, in which the portion of the cavity of the dental element facing the stumps is open, thus rendering it necessary to close the cavity with an auxiliary cement when placing the implant.

SUMMARY OF THE INVENTION

A main objective of the present invention is to provide a superstructure of the type described above which, unlike the known superstructures, is lighter, more comfortable and less bothersome to wear.

A further objective of the invention is to provide a superstructure of the type described above which, unlike analogous structures in the field, not only does not cause the formation of uncomfortable thermal bridges in the user's mouth, but rather offers the contrary effect of alleviating temperature swings, protecting the raucous membranes from excessively hot or cold temperatures.

Another objective of the invention is to provide a superstructure of the type described above which, unlike the known superstructures, allows a considerable reduction in the production times, also with a saving of the quantity of raw material used.

These and other objectives are obtained with the superstructure for oral, dental and maxillofacial prostheses, as described hereinafter.

With respect to the known technology in the field, the superstructure of the invention offers the advantage of being lighter, more comfortable and less bothersome for the user, thanks to the significant reduction in weight due to the smaller quantities of material used for producing it.

A further advantage lies in the fact that the presence of cavities within the thickness of the superstructure of the invention creates a thermal insulation, thanks to which any discomfort deriving from contact with excessively cold and hot food and drinks is considerably mitigated.

This is also helped by the possibility of inserting thermo-insulating materials inside the same cavities. Said cavities are also advantageously suitable for receiving possible slow-release medicaments, which can therefore have direct access to the oral cavity.

Finally, the use of smaller quantities of material for producing the superstructure of the invention makes its production process more rapid and its production less costly.

BRIEF DESCRIPTION OF THE DRAWINGS

These and other objectives, advantages and characteristics are evident from the following description of a preferred embodiment of the superstructure of the invention illustrated as a non-limiting example in the figures of the enclosed drawings, in which:

FIG. 1 illustrates a sectional example of a superstructure of the known art, in particular a three-element bridge, of which one is intermediate;

FIG. 2 illustrates an example of a superstructure of the invention, corresponding to the bridge of FIG. 1, but with a hollow intermediate element;

DETAILED DESCRIPTION OF THE DRAWINGS

Figure 3:
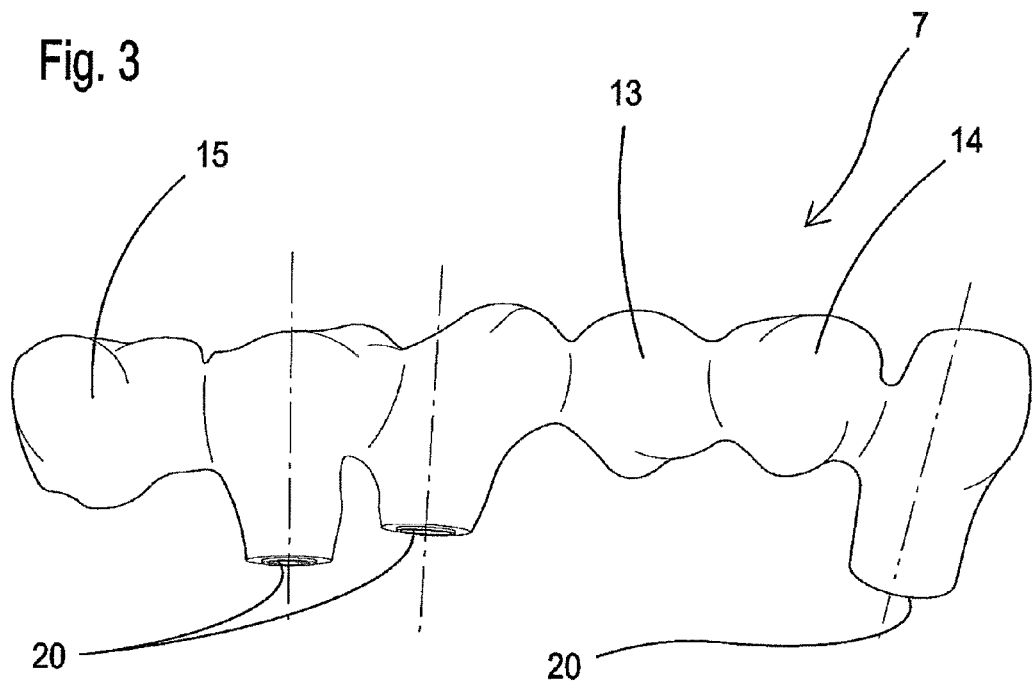
FIG. 3 illustrates a front view of another example of a superstructure of the invention, with various intermediate elements.

The superstructure 1 of the known art illustrated in FIG. 1 is composed of a bridge with three dental elements, of which the side or outer elements 2 and 3 serve for anchoring the bridge to the implant or respective stumps 4 and 5, whereas the intermediate dental element 6 is produced as a filled or solid body.

As the production material of the superstructure 1 is normally a metal alloy, the solid composition of the intermediate dental element 6 undesirably increases the overall weight of this known superstructure as a whole, making it uncomfortable to use. Furthermore, the solid structure of the superstructure 1 creates a thermal bridge, responsible for the transmission of heat and low temperatures of the mucous membranes of the mouth.

In order to overcome these drawbacks, the superstructure 7 of the invention illustrated in FIG. 2, also in the form of a three-element bridge, has an intermediate dental element 8 which is distinguished by the presence of an emptying or cavity 9 within its thickness. Hence the superstructure 7 is, as a whole, lighter than that 1 of the traditional type, without however jeopardizing its performances, in particular its resistance to use. In this way, the superstructure 7 of the invention is more comfortable to wear in the mouth and less bothersome, also thanks to the thermal insulation created by the presence of the above-mentioned internal cavity 9.

Figure 6:
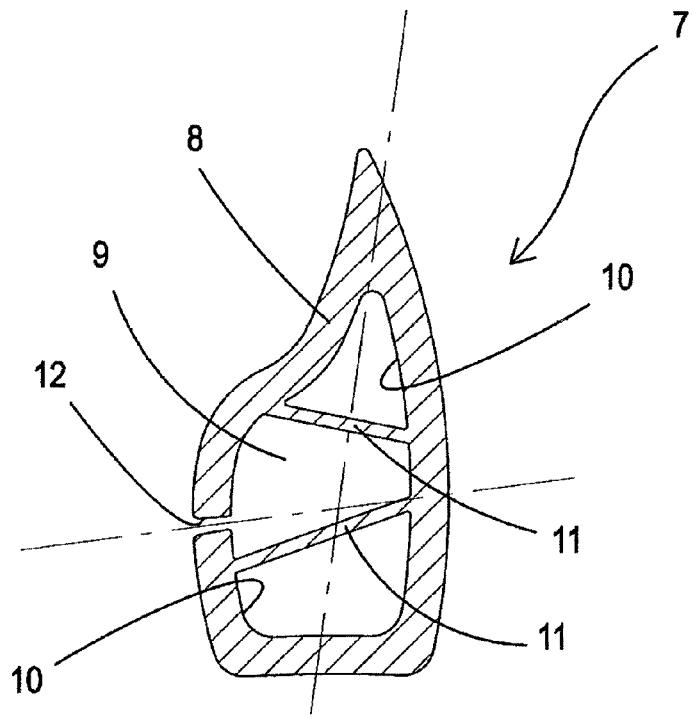
FIG. 6 illustrates the detail of an intermediate dental element of the superstructure of the invention, provided with reinforcing ribs, in a transversal vertical section.

If preferred, in order to be able to introduce a medicament or thermo-insulating material into this cavity 9, the intermediate dental element 8 of the superstructure of the invention can comprise a small hole 12, as illustrated in FIG. 6.

Furthermore, on the internal walls 10 of the cavity 9 of the intermediate dental element 8 of the superstructure 7 of FIG. 6, there are reinforcements, in the example illustrated by ribs 11 suitable for resisting chewing stress.

A stratification process is used for the production of the superstructure 7 of the invention, preferably with a laser technology which, among other things, has the advantage of significantly reducing the production times of the superstructure, having an intermediate element provided with the above-mentioned closed internal cavity 9.

Figure 4:
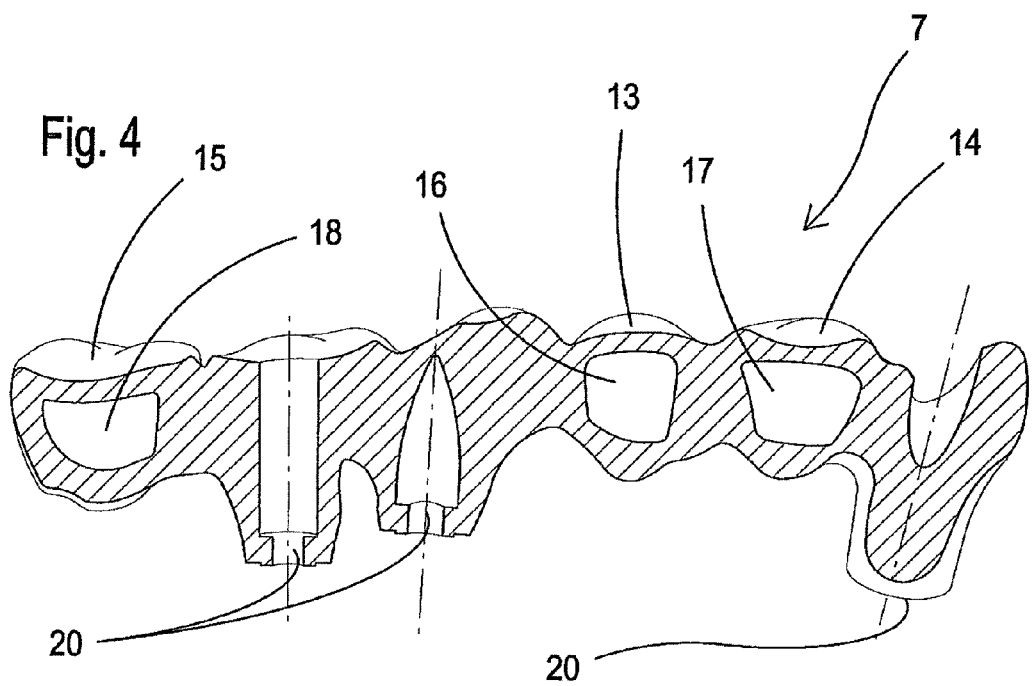
FIG. 4 illustrates the superstructure of FIG. 3 in a longitudinal vertical section.

The superstructure of FIGS. 3 and 4 comprises dental elements 20 which serve for anchoring it to the implant or respective stumps, a plurality of intermediate dental elements 13 and 14, in addition to an extension dental element 15. The above dental elements 13, 14 and 15 are distinguished by the presence of respective internal cavities 16, 17 and 18, corresponding to the cavity 9 of the superstructure 7 of FIG. 2. The extension dental element 15, moreover, can also have reinforcing ribs, similar to those described with reference to the intermediate dental element 8.

Figure 5:
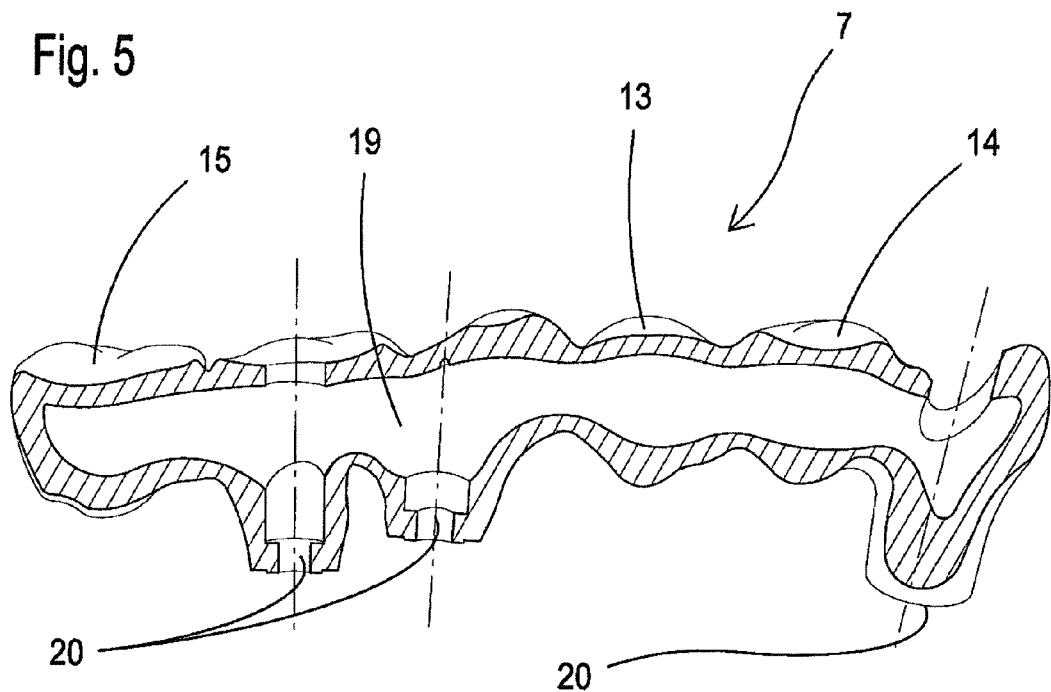
FIG. 5 illustrates a variant of the superstructure of FIG. 3 in a longitudinal vertical section.

In the variant of FIG. 5, the superstructure of FIG. 4 is modified by the presence, within its thickness and along the whole longitudinal development of the same superstructure, of a single continuous cavity 19, closed with respect to the outside and which puts at least the dental elements 13, 14 and 15 in communication with each other. This further contributes to lightening the superstructure of the invention as a whole, enhancing its lightness and the thermo-insulating properties described above.

The material with which the superstructure of the invention is produced is preferably a metal alloy (for example a Co/Cr alloy). It is also possible, however, to use different materials, provided they are compatible with the function required by the system to be implanted in the mouth, and also with the stratification process used for producing it.

Having thus described some preferred exemplary embodiments of the device of the present invention in accordance with the principles of the present invention, it should be apparent to those skilled in the art that various additional objects and advantages have been attained by the invention and that a variety of modifications can be made within the scope of the present invention, being limited by the following appended claims only.

The invention claimed is:

1. A superstructure for oral, dental and maxillofacial prostheses, comprising:
    a bridge provided with at least one anchoring dental element (2,3,20) for anchoring said bridge to a corresponding implant or stump; and
    at least one additional dental element (8,13,14,15) secured to said at least one anchoring dental element (2,3,20),
    wherein said at least one additional dental element (8,13,14,15) has an internal hollow portion defining, inside said at least one additional dental element (8,13,14,15), a first cavity (9,16,17) which is closed on a side thereof facing said implant or stump, and
    wherein said bridge comprises at least one extension dental element (15) having a second cavity (18) which is closed on a side thereof facing said implant or stump.

2. The superstructure according to claim 1, wherein said superstructure has a continuous single cavity (19) which develops continuously at least inside said anchoring dental element, said additional dental element, and said at least one extension element (13,14,15,20), said continuous single cavity comprising said first cavity (9, 16, 17) and said second cavity (18).

3. The superstructure according to claim 1, wherein at least one of said first cavity (9,16,17) or said second cavity (18) has an internal wall (10) provided with one or more reinforcing ribs (11).

4. The superstructure according to claim 1, wherein a side wall of said at least one additional dental element (8,13,14,15) has an opening (12) to providing access to said first cavity (9).

* * * * *